United States Patent [19]

Fakhri

[11] Patent Number: 5,207,231
[45] Date of Patent: May 4, 1993

[54] ELECTRO-THERAPY APPARATUS AND METHOD OF TREATING DENTAL DISEASE

[76] Inventor: Omar Fakhri, 115 Broadley Street, London NW8, Great Britain

[21] Appl. No.: 689,808
[22] PCT Filed: Nov. 16, 1989
[86] PCT No.: PCT/GB89/01356
  § 371 Date: Jun. 13, 1991
  § 102(e) Date: Jun. 13, 1991
[87] PCT Pub. No.: WO90/05561
  PCT Pub. Date: May 31, 1990

[30] Foreign Application Priority Data

Nov. 17, 1988 [GB] United Kingdom .................. 8826903
Jun. 15, 1989 [GB] United Kingdom .................. 8913774

[51] Int. Cl.⁵ ............................................. A61N 1/32
[52] U.S. Cl. .................................... 128/787; 128/791; 128/419 R
[58] Field of Search ............... 128/419 R, 421, 419 S, 128/791, 802, 787; 604/20

[56] References Cited

U.S. PATENT DOCUMENTS

| | | | |
|---|---|---|---|
| 500,172 | 6/1893 | Washburn | 128/791 |
| 566,103 | 8/1896 | Waite | 128/419 R |
| 569,380 | 10/1896 | Hollingsworth | 128/787 |
| 999,945 | 8/1911 | Aub | 128/791 |
| 2,055,540 | 9/1936 | Karnofsky | 128/787 |
| 3,207,161 | 12/1965 | Dietz | 128/787 |
| 3,234,942 | 2/1966 | Simor | 128/787 |
| 3,502,076 | 3/1970 | Bertolini | 128/787 |
| 4,149,533 | 4/1979 | Ishikawa et al. | 604/20 |
| 4,161,174 | 6/1979 | Mercuri | 128/641 |
| 4,301,794 | 10/1981 | Tapper | 128/419 R |
| 4,323,073 | 4/1982 | Ferris | 128/419 R |
| 4,503,863 | 3/1985 | Katims | 128/421 |
| 4,537,195 | 8/1985 | McDonnell | 128/422 |
| 4,709,700 | 12/1987 | Hyrman | 128/419 S |
| 4,844,075 | 7/1989 | Liss et al. | 128/419 R |
| 4,865,048 | 9/1989 | Eckerson | 128/791 |
| 4,881,526 | 11/1989 | Johnson et al. | 128/421 |

Primary Examiner—Lee S. Cohen
Assistant Examiner—Jeffrey R. Jastrzab
Attorney, Agent, or Firm—Young & Thompson

[57] ABSTRACT

Electro-therapy apparatus is provided comprising first and second electrodes 22, 24 at least the first of which is shaped to provide a substantial area of engagement with an outer surface region of the human head or face, and a current source 12 connectable with the first and second electrode so as to thereby pass current through at least a portion of the human head.

6 Claims, 4 Drawing Sheets

ELECTRO-THERAPY APPARATUS AND METHOD OF TREATING DENTAL DISEASE

The present invention relates to an apparatus and method for treating the human body by way of electro-therapy.

DISCLOSURE OF THE INVENTION

The invention seeks to provide such apparatus which is easily attached to the body and can easily be operated by the patient or some other party administering the treatment.

According to the present invention there is provided apparatus for treating the human body by means of electro-therapy, the apparatus comprising first and second electrode means arranged for engagement with respective spaced portions of the human head, at least the first electrode means being shaped to provide a substantial area of engagement with an outer surface region of the human head, and a current source connectable with the first and second electrode means so as to thereby pass current through at least a portion of the human head.

According to the present invention there is provided a method for ameliorating auto-immune diseases such as exophthalmos, uveitis, retinal vasculitis, diabetes melitus, thyrotoxicosis, ulceractive colitis and other such diseases, and disease resulting from impaired cerebral circulation such as C.V.A., and/or cerebral oedema and/or congestions and/or dental diseases, comprising passing a direct electric current through the human head. In particular, the dental diseases which can be treated comprise pulpitis and perirepical abscess.

The auto-immune diseases mentioned are by way of example only, there being, as is well known, a total of upwards of eight different diseases in the category of auto-immune diseases.

BRIEF DESCRIPTION OF THE DRAWINGS

The invention is described further hereinafter, by way of example only, with reference to the accompanying drawings in which.

BEST MODE OF CARRYING OUT THE INVENTION

Figure 1:
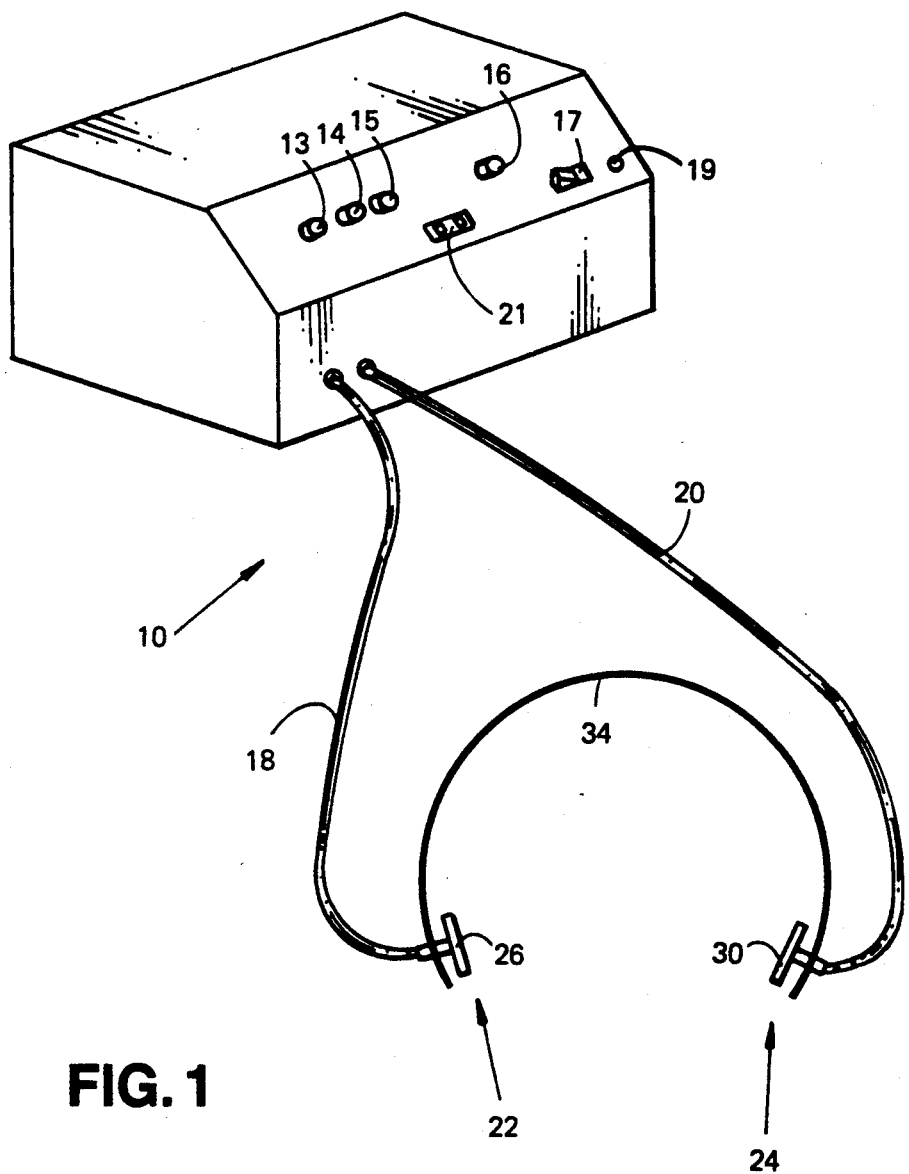
FIG. 1 is a perspective view of apparatus embodying the present invention.

A current supply control unit 12 supplies a d.c voltage in the range 0-15 v across the electrodes 22, 24 and current in the range 0-10 mAmp. The electrodes are electrically connected to the unit 12 by way of respective leads 18, 20. The unit 12 includes a battery 44, shown in FIG. 3, for providing the d.c voltage but may alternatively included a transformer for stepping down a main voltage supply and a rectifier for converting the a.c voltage to the d.c voltage required at the electrodes 22, 24.

The electrodes are located at respective ends of a resilient head-band 34 by means of which the electrodes can be located on respective sides of the tempro frontal region of the human head.

Figure 2A:
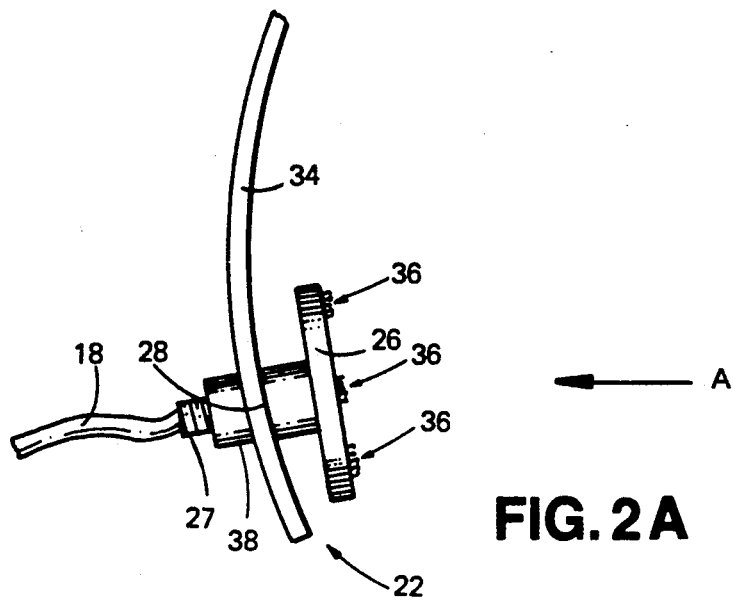
FIG. 2A illustrates a front elevational view of one of the electrode means of FIG. 1.
Figure 2B:
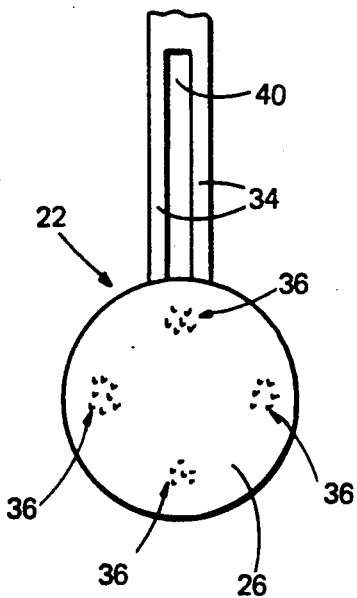
FIG. 2B is a side elevational view in the direction of arrow A of FIG. 2A.

FIG. 2 illustrates one 22 of the electrodes located at one end of the head-band 34. The headband 34 has a slot 40 (FIG. 2B) extending along the length thereof through which slot 40 a threaded boss attached to the electrode 26 extends. The extension of the threaded boss 27 through the slot 40 is limited by a shoulder portion 28 having transverse dimensions greater than the width of the slot 40. A screw lock member 38 is screwed onto the threaded boss 27 such that the headband 34 becomes clamped between the screw lock 38 and the shoulder portion 28 of the boss 27. Electrical connection to the electrode 26 is made by way of the power lead 18 attached through the centre of the threaded boss 27. Thus, the location of the electrode 26 along the length of the headband 34 can be adjusted so suit the particular dimensions of the patient's head and so ensure that the electrodes are in electrical connection with a correct surface region of the head.

Figure 2C:
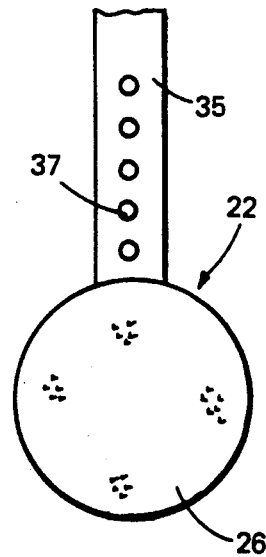
FIG. 2C is a side elevational view of an electrode means attached to a further type of headband to that in FIG. 2B.

The headband 35 in FIG. 2C includes a plurality of apertures 37 at each end thereof through which the threaded boss 27 can be received so as to allow for the adjustment of the location of the electrode means on the headband.

As an alternative to the threaded boss 27, the electrode means may be located and/or secured on the headband by means of a two-part press fit electrode connector. As such the two parts are pressed together sandwiching the headband therebetween. Such a press fit arrangement is particularly of use with the headband of FIG. 2C.

As illustrated in FIGS. 2A and 2B, the surface of the electrode 26 for location adjacent to the human head includes a plurality of hook-like attachment means 36. Alternatively, pin type attachment means are provided to secure a sponge against lateral, sliding movement on the electrode face. In use, a disc-like sponge having dimensions similar to that of the electrode 26 and having been impregnated with electrically conductive gel is attached to the electrode 26 by way of the attachment means 36. On completion of the treatment, the sponge can be removed and replaced by a new sponge when the apparatus is next used.

An on/off rheostat switch 16, for controlling the current supply to the electrodes, is provided on a front panel of the unit adjacent three timer control knobs 13, 14, 15. The timer control knobs 13, 14, 15 can be set to allow the unit 12 to supply current to the electrodes 22, 24 for two variable respective time periods with a variable rest period therebetween. Additionally, the unit also includes means for controlling the magnitude of the current in response to expiry of all or a pre-determined part of at least one of the set time periods.

The current supply control unit 12 includes circuitry for allowing the patient to receive the treatment without having to make any manual adjustment of the on/off rheostat switch 16 or other control devices. However, manual override is possible if the patient feels that the magnitude of the current supply is too large or too small.

Primarily, the timer is set by means of the control knobs 13, 14, 15 so as to determine the length of the treatment period. The treatment period is advantageously divided into a plurality of phases and the time span of each phase can be set by means of the respective control knobs 13, 14, 15.

The unit 12 includes a time initiation switch 17 which controls commencement of the predetermined time period set by way of the control knobs 13, 14, 15. An LED 19 is provided to indicate that the unit is operating under the control of the timer unit. A liquid crystal display 21 is also provided to indicate the period remaining of the treatment session.

The current supply control unit 12 controls the current supply in such a way that, on commencement of the treatment, the magnitude of the current can be increased gradually manually until the patient experiences a tingling sensation. Once a suitable magnitude of current has been reached, the timer initiation switch 17 is closed and the current is supplied for the preset time periods. A steady d.c. current is then supplied to the patient by way of the electrodes 22, 24 for a pre-determined first phase of the operation. The first phase generally lasts between 1 to 10 minutes. On completion of the first phase, the current supply control unit 12 gradually reduces the magnitude of the current until no current is caused to flow between the electrodes 22, 24. A rest phase is then initiated whereby no current is supplied to the patient and the polarity of the electrodes 22, 24 is reversed by means of a polarity switch 48 in the unit 12. On completion of the rest phase, a second phase is commenced in which the current is gradually increased in magnitude to the same level set by the patient for the first phase. However, a steady direct current is supplied in the opposite direction to that of the first phase.

The first, rest and second phases can be set to last for between 1 to 10 minutes. On completion of the second phase, the control unit 12 causes the magnitude of the current to decrease gradually to zero. At this point, the treatment session is complete.

Thus, the current supply control unit 12 controls the magnitude and the direction of the current in response to a control signal related to the treatment time of the various phases as preset by the patient or person administering the treatment. Of course, the method of the invention may be performed by manual control and reversal of the current supplied to the patient.

Figure 6:
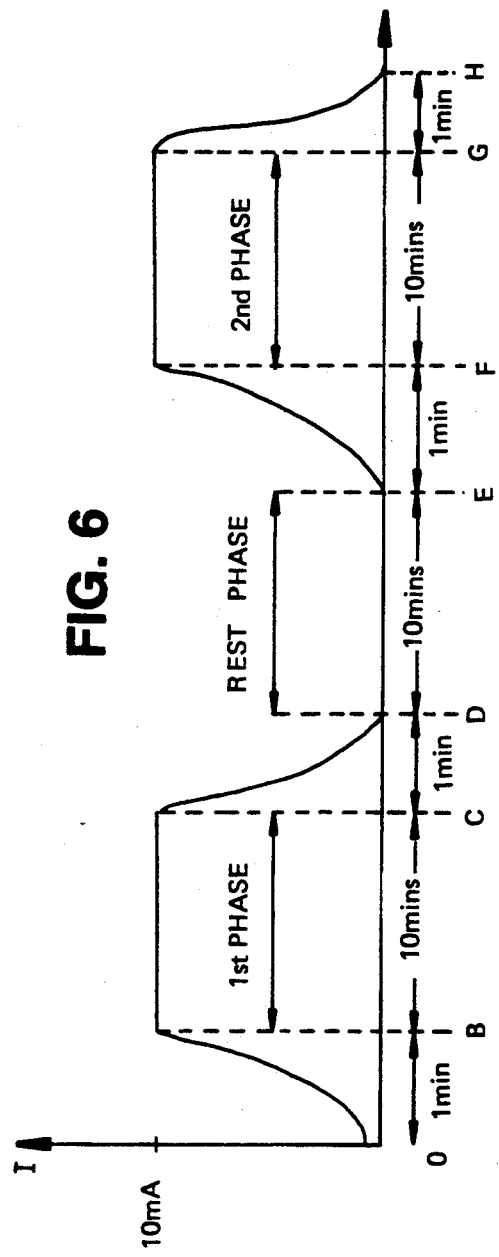
FIG. 6 is a graphical representation of one example of a treatment session according to the present invention.

FIG. 6 is a representation of the variation of the supply current during one example of a treatment session administered according to the invention. The interphase treatment periods are shown not to scale for reasons of clarity.

It is assumed that the duration of the first, rest and second phase of treatment has been set by way of controls 13, 14, 15 and during the period O-B, the magnitude of the current I is gradually increased manually by way of the rheostat switch 16 until the patient experiences a tingling sensation. From B-C, the device is in its first phase and a steady state direct current is supplied at, for example, a value of 10 mAmp and for 10 minutes. From C-D, the magnitude of the current is gradually decreased to zero under the control of the unit 12. From D-E, no current is supplied for 10 minutes and the polarity of the electrodes is reversed. From E-F, the magnitude of the current is gradually increased under the control of unit 12 until it reaches a magnitude corresponding to that of the first phase. From F-G, a steady state direct current is supplied for 10 minutes and from G-H, a gradual decrease in the magnitude of the current is effected by unit 12 so as to terminate the session. The first, rest and second phases could of course be provided for a period less than 10 minutes.

Figure 3:
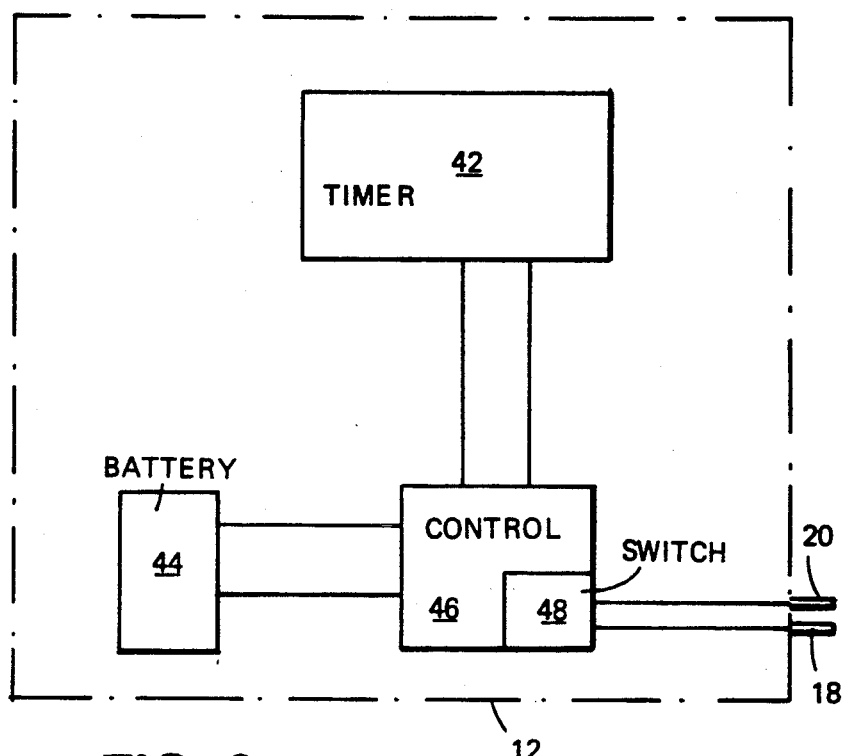
FIG. 3 is a block diagram of the circuitry of the current supply control unit 12.

FIG. 3 is a block diagram showing the circuitry of the control unit 12 and comprises a battery 44, a current control unit 46, a timer unit 42 and a current polarity switch 48 provided as part of the current control unit 46. The battery 44 is connected to the current control unit 46 so as to act as a current source therefore and the current control unit 46 receives controlling signals from a timer unit 42. The timer unit 42 is associated with switch means (not shown) on the unit 12 by means of which the time period of the various phases of treatment can be pre-set. The current control unit 46 supplies an outward current to the electrical leads 18, 20 by way of the polarity switch 48. Thus, in operation, the time periods of the various phases of the treatment are pre-set in the timer unit 42 and the current control unit 46 is switched on and the current either manually or otherwise increased until the patient experiences a tingling sensation. The phase control regimes of the timer unit 42 then control the subsequent operation of the current control unit 46 and polarity switch 48.

Figure 4:
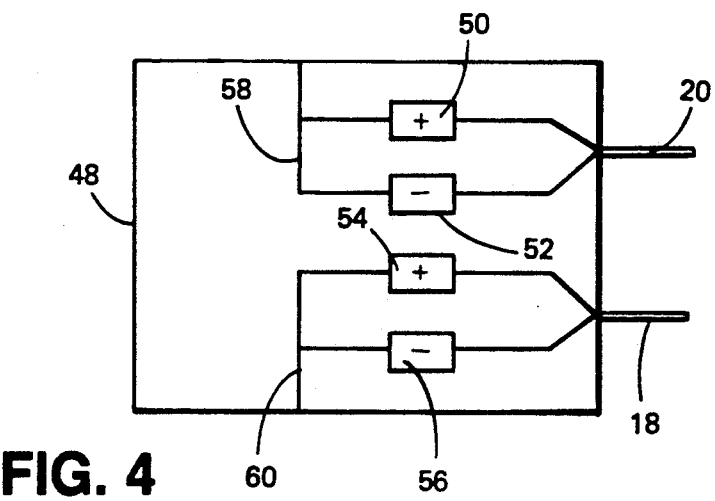
FIG. 4 is a block diagram of the polarity switching circuit of FIG. 3.

FIG. 4 illustrates further detail of the polarity switch 48 of FIG. 3. The polarity switch 48 comprises current switches 50, 52, 54, 56, the switches 50, 52 being connected to the current supply lead 20 and the switches 54, 56 being connected to the supply lead 18. A control signal is fed to the switches 50, 52 by way of a common control line 58 and, similarly, a control line 60 feds a control signal to the switches 54, 56.

The switches 50, 52, 54, 56 may comprise transistor switches or magnetic relay switches and one 50, 54 of each of the pairs provides a positive supply to the output leads 18, 20, and the other 52, 56 of the pairs supplies a negative supply to the leads 18, 20.

The operation of the polarity switch 48 is as follows:

The switch control signal lines 58, 60 are fed with opposite signals such that when the signal on 58 is a "1" or "high" the signal on the line 60 is "0" or "low".

In such a state, the switches 50, 56 are turned on and the switches 52, 54 are held in an "off" state such that the lead 20 comprises the anode and the lead 18 comprises the cathode. However, when, during the rest phase, the polarity of the supply is switched, a control signal "0" or "low" is supplied to line 58 by the current control unit 46 and a "1" or "high" signal is applied to control line 60 by way of the current control unit 46. This causes the gates 50, 56 to be switched to an "off" state and the gates 52, 54 to be switched on. As such, the lead 18 then becomes the supply for the anode and the lead 20 become the supply for the cathode.

Thus, when the second phase of treatment commences the polarity of the electrodes has been reversed.

In use, the electrodes are received by respective sides of the tempro frontal region of the head of the patient and the unit 12 is switched on by means of the rheostat switch 16. The time periods for the respective phases of operation are set by way of the controls 13, 14, 15. The patient then gradually increases the magnitude of the current and voltage supplied at the electrodes 22, 24 until a tingling sensation is experienced. Once the required magnitude of current is reached, as indicated by the tingling sensation, the control switch 17 is closed so that the pre-set time periods commence and the subsequent control of the unit 12 is achieved in response to the passage of these time periods. As mentioned above current control circuitry ensures that the magnitude of the voltage developed at the electrodes 22, 24 is reduced gradually once the treatment is terminated.

Within the scope of the present invention electrodes are provided which are shaped to provide a substantial area of engagement by a human tooth or teeth.

Figure 5:
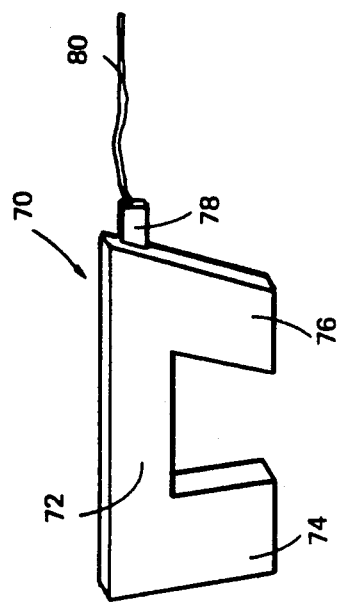
FIG. 5 is a perspective view of the second electrode means of the present invention arranged to be engaged with a tooth.

FIG. 5 illustrates an electrode for engagement by the tooth or teeth. The electrode 70 comprises a resilient carbonized rubber member. A current supply lead 80 is electrically connected to the electrode 70 by way of a connector 78.

The electrode 70 comprises a laterally extending portion 72 having at each end thereof a downwardly extending side portion 74, 76. The distance for separation of the foot region of the side portion 74, 76 is chosen to be less than the width of a human tooth so that when the separation thereof is increases so as to attach the electrode to the tooth, the resiliency of the electrode side portions causes the electrode 70 to grip the tooth. Alternatively however, the electrode may be provided as a carbonized rubber bit which is arranged to be retained in the patient's mouth and in contact with the particular tooth by way of the biting action of the jaw. The other of the electrodes is then connected externally close to the affected tooth. As such, the external electrode may be held in position by the patient or by way of clip means.

The tooth electrode may also comprise a metal electrode shaped as in FIG. 5, or otherwise, and which is covered by a carbonized rubber sleeve.

The electrodes of the present invention for external contact to the head comprise stainless steel electrodes and as an alternative to the impregnated sponge outlined above, the contact surface of the electrode may be arranged for attachment of a gauze or lint cloth soaked in the gel or a saline solution. Provision of an interface between the skin and the stainless steel electrode serves to prevent metal ions from penetrating the skin and causing dermatitis.

The apparatus illustrated in FIGS. 1 and 2A and 2B is particularly useful for the treatment of auto-immune disease and cerebral oedema and the use of electro-therapy in the treatment of these diseases and dental diseases is novel. It was found that direct current in the range stated in this description is of value in the treatment of such diseases.

Administering the treatment for the correct period of time is important since supplying the current for an insufficient period of time will not achieve the purpose. Also, over exposing the patient to the current will be harmful. The addition of a preset timer unit ensures the application of the current for the required period of time. A particular feature of the apparatus is the supply unit, the specification of which is based on research carried out to find the optimum current to treat such conditions.

The different types of electrodes were designed to conform with the requirements of the therapy methods, and are made of stainless steel for the following reasons. Firstly to prevent rusting of the electrodes by the frequent application of the electrically conductive gel, and secondly since stainless steel is less ionizable than other metals which, if ionized, might penetrate the skin by iontophoresis which will cause dermatitis.

The administering of electro-therapy as described above is particularly advantageous since the supply of current in one direction for the whole treatment period may burn the skin at the location of the negative electrode and the reversal of the polarity of the electrodes during the treatment overcomes this problem. However, a sudden change of polarity causes the patient to suffer an electric shock and also a headache. The magnitude of the current is therefore reduced gradually so as to terminate supply of the current. The application of the current in the opposite direction to that as in the first phase, immediately after termination of the first phase, commonly causes some burning sensation and pain and it is therefore advantageous to provide the rest phase before proceeding with the further current supply of the second phase.

The electrodes of FIGS. 1, 2A and 2B are placed on the tempro frontal region of the head, as mutually opposite locations, to ensure that current passes between the two electrodes by way of the eye, the orbital tissue, the pituitary gland, the hypothalamus and part of the brain, in particular the deep-brain region.

The passage of the current way found to be of benefit in the disease described for the following reasons:

Improved circulation is achieved by the release of Calcitonine Gene Related Peptide (CGRP), a potent vaso dilator;

By increasing tissue permeability, and so producing a decongestive effect and remove the oedema in the tissue through which the current is passing; and By interfering with the release of stress hormones and other factors which initiate the auto-immune process.

However, the invention is not to be regarded as dependent in any way on the above explanations.

The passage of the current through the temple was found to have the same effect as the administering of steroid and immunosuppressant drugs currently used to treat auto-immune diseases, which drugs commonly have dangerous side effects and are expensive. The use of such drugs can therefore be avoided by using the treatment of the present invention. Also, the treatment provides for decongestion and removal of excess tissue fluids such as in exophthalmos, cerebral oedema and also as a substitute for complicated operations.

For patients with C.V.A., auto-immune diseases including those which affect the eyes and cerebral oedema, the electrodes are placed on the tempro frontal region as described hereinbefore. The current supply unit is then switched on and a current flow initiated and increased until the patient starts to feel a tingling sensation without discomfort. As an example, the time period for the first phase, the rest phase and the second phase is set at 10 minutes each phase. The treatment is repeated 2-3 times a week for four weeks depending on the severity of the patient's condition. The frequency of administering the treatment sessions is then reduced to one session per week for four weeks and thereafter to one session every two weeks. The frequency of the provision of the treatment sessions can of course be varied to suit the particular requirements of a particular patient.

In the treatment of dental diseases, the carbonized rubber electrode is placed onto the effected tooth and may be secured in place by biting. The electrode for external attachment to the head is then located below the affected tooth if this tooth is in the lower jaw or at a location adjacent the tooth if the affected tooth is located in the upper jaw. The current is then supplied for a first treatment period of 10 minutes and then gradually reduced and so terminated in response to the first treatment period expiring. The treatment session is repeated two times per week. The treatment achieves relief of pain in the case of pulpitis after the end of the first treatment session. However, it may be necessary to continue the treatment for two-three more sessions and in cases of perirepical abscess, the therapy may need to be continued two times per week for four weeks or until the abscess is resolved.

Although the invention is not be regarded as dependent in any way on the following explanation, it is thought that the method of the invention acts to ameliorate pulpitis by reducing oedema and so releasing pressure on the nerve and causing the associated pain to subside.

In ameliorating perirepical abscess, the circulation is improved to enhance destruction of the infection and so render analgesics, antibiotics and root canal operations unnecessary.

What is claimed is:

1. A method of treating dental disease by electrotherapy, comprising applying to a human tooth affected with such a disease electrode means shaped to provide a substantial area of engagement with the tooth, and passing a direct electric current through the tooth via said electrode means for a predetermined period of time, wherein said disease is pulpitis and wherein said electric current is applied for 10 minutes and then gradually reduced.

2. Apparatus for treating dental diseases, comprising a resiliently deformable electrode for attachment to a tooth, a second electrode shaped to provide substantial engagement with an outer surface region of the human head, and a source of direct electrical current connected with the resiliently deformable and second electrodes to pass direct current therebetween, wherein said resiliently deformable electrode is U-shaped with side portions spaced apart a distance less than the width of a human tooth, whereby said side portions resiliently grip a said tooth between them.

3. Apparatus as claimed in claim 2, in which said resiliently deformable electrode is of resiliently deformable carbonized rubber.

4. A method of treating dental disease by electrotherapy, comprising applying to a human tooth affected with such a disease electrode means shaped to provide a substantial area of engagement with the tooth, and passing a direct electric current through the tooth via said electrode means for predetermined period of time, wherein said disease is perirepical abscess and said method is practiced at least two times per week for at least four weeks.

5. A method of treating dental disease by electrotherapy, comprising applying to a human tooth affected with such a disease electrode means shaped to provide a substantial area of engagement with the tooth, and passing a direct electric current through the tooth via said electrode means for a predetermined period of time, and increasing the current gradually at the beginning of treatment and decreasing the current gradually at the end of treatment.

6. A method of treating dental disease by electrotherapy, comprising applying to a human tooth affected with such a disease electrode mens shaped to provide a substantial area of engagement with the tooth, and passing a direct electric current through the tooth via said electrode means for a predetermined period of time, wherein the current is supplied at a voltage of up to 15 volts and a current of up to 10 mAmps.

* * * * *